United States Patent
Lauraeus et al.

(10) Patent No.: US 10,538,735 B2
(45) Date of Patent: *Jan. 21, 2020

(54) MATRIX AND COMPOSITION FOR MICROBIAL CULTURE OF GRAM-POSITIVE BACTERIA

(71) Applicant: UPM-KYMMENE CORPORATION, Helsinki (FI)

(72) Inventors: Marko Lauraeus, Vihti (FI); Antti Laukkanen, Helsinki (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 14/368,067

(22) PCT Filed: Dec. 18, 2012

(86) PCT No.: PCT/FI2012/051264
§ 371 (c)(1),
(2) Date: Jun. 23, 2014

(87) PCT Pub. No.: WO2013/093197
PCT Pub. Date: Jun. 27, 2013

(65) Prior Publication Data
US 2014/0349377 A1    Nov. 27, 2014

(30) Foreign Application Priority Data
Dec. 22, 2011  (FI) .................................... 20116316

(51) Int. Cl.
*C12N 1/22* (2006.01)
*C12N 11/12* (2006.01)
*C12N 11/04* (2006.01)
*C08L 1/02* (2006.01)
*C12N 1/20* (2006.01)

(52) U.S. Cl.
CPC .................. *C12N 1/22* (2013.01); *C08L 1/02* (2013.01); *C12N 1/20* (2013.01); *C12N 11/04* (2013.01); *C12N 11/12* (2013.01); *C12N 2500/34* (2013.01)

(58) Field of Classification Search
CPC ..................................... C12N 1/22; C12N 1/20
See application file for complete search history.

(56) References Cited

U.S. PATENT DOCUMENTS

| 2,978,446 | A | | 4/1961 | Battista et al. | |
|---|---|---|---|---|---|
| 3,775,252 | A | * | 11/1973 | Kinsel | C12N 1/16 426/60 |
| 5,254,471 | A | | 10/1993 | Mori et al. | |
| 5,963,419 | A | * | 10/1999 | Tanaka | H01G 9/02 361/512 |
| 9,593,304 | B2 | * | 3/2017 | Laukkanen | C12N 5/0062 |
| 2007/0172938 | A1 | | 7/2007 | Deguchi et al. | |
| 2008/0146701 | A1 | * | 6/2008 | Sain | B82Y 30/00 524/9 |
| 2009/0123990 | A1 | * | 5/2009 | Bergmaier | C12N 1/063 435/252.9 |
| 2011/0015387 | A1 | * | 1/2011 | Schuth | C08B 1/003 536/124 |

FOREIGN PATENT DOCUMENTS

| EP | 0243151 A2 | 10/1987 | |
|---|---|---|---|
| WO | 9831785 A1 | 7/1998 | |
| WO | 2005/083056 A1 | 9/2005 | |
| WO | 2009126980 A1 | 10/2009 | |
| WO | WO 2010135234 A2 * | 11/2010 | ............... C12N 1/20 |
| WO | 2012056109 A2 | 5/2012 | |

OTHER PUBLICATIONS

'Matrix' in: Oxford Dictionaries [online]. 2018. [retrieved on Mar. 28, 2018]. Retrieved from the Internet: <URL: https://en.oxforddictionaries.com/definition/matrix>. (Year: 2018).*
Zhang, J et al. Chemically defined media for commercial fermentations. Appl. Microbiol. Biotechnol. 1999. 51: 407-421. (Year: 1999).*
Bhattacharya et al., "Nanofibrillar cellulose hydrogel promotes three-dimensional liver cell culture", Journal of Controlled Release, 2012, vol. 164, pp. 291-298.
Deguchi et al., "Preparation and characterisation of nanofibrous cellulose plate as a new solid support for microbial culture", Soft Matter, 2007, vol. 3, pp. 1170-1175.
Tsudome et al., "Versatile Solidified Nanofibrous Cellulose-Containing Media for Growth of Extremophiles", Applied and Environmental Microbiology, 2009, pp. 4616-4619.
Finnish Search Report, dated Sep. 5, 2012, from corresponding FI application.
International Search Report, dated Apr. 2, 2013, from corresponding PCT application.
M. Pääkkö, et al., "Enzymatic Hydrolysis Combined with Mechanical Shearing and High-Pressure Homogenization for Nanoscale Cellulose Fibrils and Strong Gels", Biomacromolecules, Aug. 2007, 1934-1941.
Ung-Jin Kim, et al., "Thermal decomposition of dialdehyde cellulose and its nitrogen-containing derivatives", Thermochimica Acta, 369 (2001) 79-85.
The Merck Index: An encyclopedia of chemicals, drugs, and biologicals, 1996.
Seibutsu-kogaku Kaishi, 2011, 89(4), 195-199.
Shan-shan Lin, et al., "Optimization of medium composition for the production of alkaline β-mannanase by alkaliphilic *Bacillus* sp. N16-5 using response surface methodology", Appl Microbiol Biotechnol (2007) 75: 1015-1022.

(Continued)

*Primary Examiner* — Renee Claytor
*Assistant Examiner* — Susan E. Fernandez
(74) *Attorney, Agent, or Firm* — Nixon Peabody LLP

(57) ABSTRACT

A composition for fermentation or microbial culture of gram-positive bacteria, includes fibril cellulose and at least one nutrient source including at least one carbon source, at least one nitrogen source, at least one phosphorus source, at least one mineral source and at least one trace element source.

17 Claims, 4 Drawing Sheets

(56) References Cited

OTHER PUBLICATIONS

Microbiology, Basic Master series, Omsha, 2006, 1st Edition, p. 55.
Fangfang Wu, et al., "Experimental Study on Bioremediation of Contaminated Soil", Journal of the Association of Materials Engineering for Resources, 2002, vol. 15, No. 2, p. 59-65.
Notice of Reasons for Refusal from corresponding Japanese Patent Application No. 548119/2014, dated Nov. 8, 2016, with English Translation.
Moreira, S. et al.; "BC nanofibres: In vitro study of genotoxicity and cell proliferation"; Toxicology Letters, vol. 189, pp. 235-241; Jun. 12, 2009; (7 pages).
Kondo, T.; "New Aspects of Cellulose Nanofibers"; Mokuzai Gakkaishi, vol. 54, No. 3, pp. 107-115; 2008; with English translation (17 pages).
Pitkanen, M. et al.; "Nanofibrillar cellulose—in vitro study of cytotoxic and genotoxic properties"; TAPPI, International Conference on Nanotechnology for the Forest Products Industry; Sep. 27-29, 2010 (16 pages).
Decision of Declining Amendments—from Japanese Patent Application No. 548121/2014, dated Apr. 3, 2018 with English Translation.
Notice of Reasons for Refusal—from Japanese Patent Application No. 548121/2014, dated Apr. 3, 2018 with English Translation.
Journal of Textile Engineering, 1997, vol. 50, No. 4, p. 7-11.

\* cited by examiner

MATRIX AND COMPOSITION FOR MICROBIAL CULTURE OF GRAM-POSITIVE BACTERIA

FIELD OF THE INVENTION

The invention relates to new applications of fibril cellulose in the field of microbiology. Particularly the invention relates to a composition comprising fibril cellulose for microbial culture of gram-positive bacteria and to a two-dimensional or three-dimensional matrix comprising fibril cellulose for microbial culture of gram-positive bacteria. The invention further relates to use and a method of using fibril cellulose as a matrix for microbial culture of gram-positive bacteria, and to a method for culturing gram-positive bacteria.

BACKGROUND

Hydrogel materials are used in culturing tasks where hydrophilic supporting material is needed, and for example agar type hydrocolloids are widely used in plant cell, bacterial, and fungi culturing for various microbiological purposes.

Agar is a linear and non-ionic polysaccharide consisting of D-galactose and 3,6-anhydro-L-galactose and it is produced from seaweeds. In solid cultures suspensions of microbial cells are spread onto the surface of the agar hydrogel, typically containing 1.5 wt % of agar, and nutrient fluid. The microorganisms grow and form macroscopic colonies, which can be separated and pure cultures may be obtained. The use of solid agar plates provides two-dimensional growth and the separation of colonies requires mechanical cutting etc.

Several alternatives for the use of agar plates have been proposed, for example gellan gum produced by *Pseudomonas elodea*. Gellan gum is soluble in hot water, and it forms a stiff gel upon cooling and shows improved stability at higher temperatures. Hydrogels based on gellan gum are very sensitive to nutrients and additives and require careful formulation of the medium.

In Deguchi, S. et al., Preparation and characterisation of nanofibrous cellulose plate as a new solid support for microbial culture, *Soft Matter*, 2007, Vol. 3, No. 9, s. 1170-1175, a cellulose plate is suggested for solid culture of microorganisms where the cellulose was obtained by dispersing microcrystalline cellulose in an aqueous saturated solution of $Ca(SCN)_2$ to form a complex between cellulose and calcium thiocyanate ions, followed by dissolving the cellulose by heating, and obtaining a viscous solution. Said solution was then poured into a culture dish, allowed to solidify whereby cellulose was recrystallized, followed by washing with methanol and water. After washing the gelation was fixed. The pores of the plates were filled with an appropriate nutrient fluid. *E. coli, B. subtilis*, and *S. cerevisiae* as well as *T. thermophilus* grew on the cellulose plates.

U.S. Pat. No. 5,254,471 discloses a carrier for culturing cells, made of ultrafine fibers. WO 2009/126980 discloses cellulose-based hydrogel, which contains cellulose exhibiting an average degree of polymerization of 150-6200.

Existing cell culture biomaterials do not allow transferring the hydrogel matrix with a needle without seriously damaging the cultured cells.

In connection with microbial culture, fermentation, and microbial sample storage, detection as well as enumeration and quantification of microbes, based on techniques where real-time polymerase chain reaction (PCR) is carried out, are widely used. In PCR the microbes are broken down to release their DNA and the DNA is thereafter quantified by using specific oligonucleotide primers, thermo-stable DNA polymerase and appropriate thermal cycler. Many agents and substances, present in culture materials or polymeric materials inhibit the PCR reactions and make microbial quantification unreliable. Typically such materials are used as fermentation media, culturing media, sample storage matrix, fermentation enhancers, and transportation matrix, where said materials interfere with the detection and quantification procedures.

Thus there exists a need to provide improved culture compositions, matrixes and methods for microbial culture where the disadvantages relating to the materials of state of the art can be avoided or at least substantially decreased.

SUMMARY

The invention is directed to a composition for microbial culture of gram-positive bacteria, particularly to a composition comprising fibril cellulose and a nutrient source comprising at least one carbon source, at least one nitrogen source, at least one phosphorus source, at least one mineral source and at least one trace element source. Microbial culture is understood to include here any kind of fermentation processes too.

The invention is also directed to a method for the manufacture of a composition for microbial culture of gram-positive bacteria, said method comprising the steps of
    providing fibril cellulose and at least one nutrient source comprising at least one carbon source, at least one nitrogen source, at least one phosphorus source, at least one mineral source and at least one trace element source,
    mixing said fibril cellulose with water and the nutrient source to obtain a mixture/composition.

The composition is suitably transferred or placed to an environment for culture of gram-positive bacteria.

The invention is further directed to a two-dimensional (2D) or three-dimensional (3D) matrix for microbial culture of gram-positive bacteria, said matrix comprising the composition comprising fibril cellulose and at least nutrient source comprising at least one carbon source, at least one nitrogen source, at least one phosphorus source, at least one mineral source and at least one trace element source, and living gram-positive bacteria cells.

The invention further relates to the use and to a method of using fibril cellulose and at least one nutrient source in a matrix for microbial culture of gram-positive bacteria, said method comprising the steps of
    providing living gram-positive bacteria cells,
    providing a composition comprising fibril cellulose and at least one nutrient source comprising at least one carbon source, at least one nitrogen source, at least one phosphorus source, at least one mineral source and at least one trace element source,
    incorporating said bacteria cells in and/or on the composition to provide a two-dimensional or three-dimensional arrangement.

The invention is further directed to a method for culturing gram-positive bacteria, said method comprising the steps of
    providing living gram-positive bacteria cells,
    contacting the cells with a composition comprising fibril cellulose and at least one nutrient source comprising at least one carbon source, at least one nitrogen source, at least one phosphorus source, at least one mineral source and at least one trace element source, culturing the cells in and/or on said composition in a two-dimensional or three-dimensional arrangement.

Accordingly, means for the culture and fermentation of gram-positive bacteria is provided, using a composition comprising fibril cellulose and at least one nutrient source comprising at least one carbon source, at least one nitrogen source, at least one phosphorus source, at least one mineral source and at least one trace element source, wherein the composition is in the form of a hydrogel or membrane or plate formed of the hydrogel.

Said composition may be used as a culturing media, fermentation media, as a component in fermentation media, as storage media and as transportation media for gram-positive bacteria, and also as immobilization matrix in fermentation processes of gram-positive bacteria.

Said composition may further be used as a growth enhancing additive in microbial culture and fermentation processes of gram-positive bacteria. The invention provides thus means for enhancing the growth of gram-positive bacteria.

The present invention is based on the studies on hydrogels composed of fibril cellulose, which is dispersed in aqueous environment. The fibres of fibril cellulose are highly hydrophilic due to hydroxyl functionalities of cellulose polymers and partly covered with hemicellulose polysaccharides, thus providing several advantageous properties to the culturing and fermentation media.

Microbial cells divide on and/or in the media, start to proliferate and the cell clusters start to grow spontaneously without the accumulation of cells on the bottom of the cell culture platform. The homogenous dividing of the cells in the fibril cellulose is a prerequisite for the material to function, particularly as 3D microbial culture media.

Fibril cellulose is also inert and gives no fluorescent background.

The culture media comprising fibril cellulose can be injected or pumped. Injectability is explained by the rheological properties of plant derived fibril cellulose. The injection or pumping can be performed so that the cells stay stable inside the hydrogel or matrix and are homogeneously distributed in the hydrogel or matrix after injection or pumping.

The characteristic features of the invention are presented in the appended claims.

Figure 1:
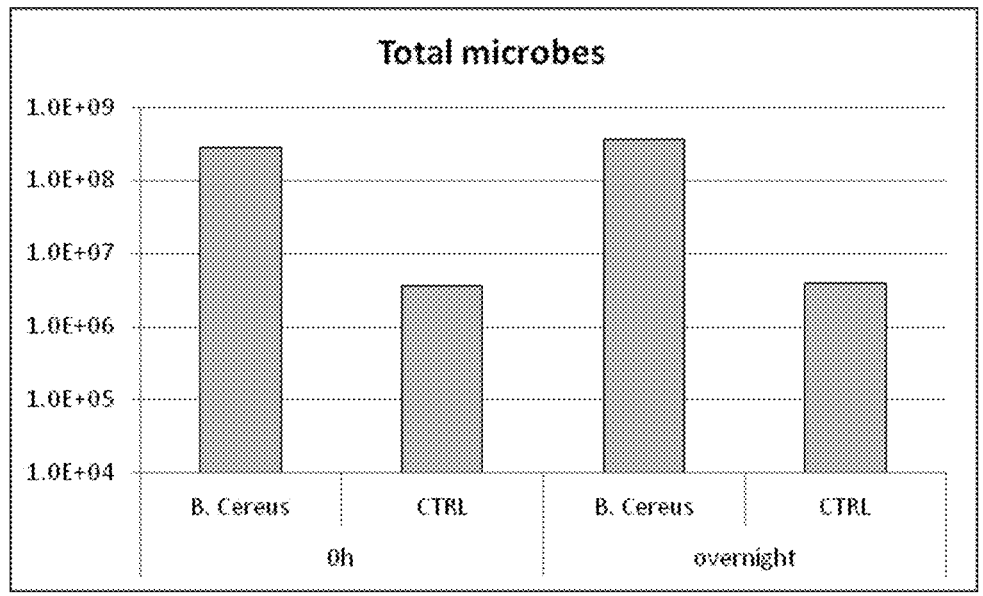
FIG. 1 illustrates graphically *Bacillus cereus* cell numbers in the beginning (0 h) and after overnight incubation with and without fibril cellulose.

FIG. 7 depicts schematic presentation of fibril cellulose hydrogel containing cells, flowing in a needle. High shear rate region (low viscosity) is located at the gel-needle interface and low shear rate region (very high viscosity) is located in the middle of the needle.

FIG. 8 depicts stability of two gravel suspensions in 0.5% native fibril cellulose hydrogel, (top row) and in 0.5% anionic fibril cellulose hydrogel (bottom row) for 17 days period. The gravel was CEN Standard sand (EN 196-1) with average particle size 1-2 mm and 2-3 mm. The samples were stored at room temperature.

DEFINITIONS

Unless otherwise specified, the terms, which are used in the specification and claims, have the meanings commonly used in the filed of microbiology and macromolecules. Specifically, the following terms have the meanings indicated below.

The term “media” or “growth media” or “culture media” refers here to nutritional environment, which is necessary for any bacterium to be propagated. The biochemical (nutritional) environment is made available as a culture medium. Culture media are employed in the isolation and maintenance of pure cultures of bacteria and are also used for identification of bacteria according to their biochemical and physiological properties.

The term “carbon source” refers to organic compounds that are metabolized by microbes to carbon for growth and development and to inorganic compounds that are used ($CO_2$) as source of carbon. Said compounds are also referred to as primary sources of carbon.

The term “nitrogen source” refers to compounds that are metabolized by microbes to nitrogen for growth and development and to inorganic compounds that are used as source of nitrogen, such as amino acids etc.

The term “phosphorus source” refers to compounds that are metabolized by microbes to phosphorus for growth and development and to inorganic compounds that are used as source of phosphorus, such as rock phosphate etc.

The term “mineral source” refers to compounds that are metabolized by microbes to minerals for growth and development and to elements or inorganic compounds that are used as source of minerals. The mineral source comprises at least the elements Na, K, Mg, Ca, Cl and S.

The term “trace element source” refers to compounds that are metabolized by microbes to minerals for growth and development and to elements or inorganic compounds that are used as source of minerals. The mineral source comprises at least the elements Cr, Mn, Fe, Se, I, Co, Ni, Cu, Zn and Mo.

The term “bioleaching” or “bioheapleaching” means here a bio-oxidation process where bacteria are utilized to convert insoluble metal compounds in ores, containing metals such as copper, gold, zinc, cobalt, nickel and uranium, to water-soluble metal compounds, which can further be converted to elemental metals.

As used herein, the term “fibril cellulose” is understood to encompass all microfibrillated celluloses (MFC) and nanocelluloses. Further, there are several other widely used synonyms for fibril cellulose. For example: cellulose nanofiber, nanofibrillated cellulose (CNF), nanofibrillar cellulose (NFC), nano-scale fibrillated cellulose, microfibrillar cellulose, or cellulose microfibrils.

In addition, fibril cellulose produced by certain microbes has also various synonymes. for example, bacterial cellulose (BC), microbial cellulose (MC), biocellulose, nata de coco (NDC), or coco de nata (CDN).

DETAILED DESCRIPTION OF THE INVENTION

It was surprisingly found that a composition comprising fibril cellulose together with at least one nutrient source comprising at least one carbon source, at least one nitrogen source, at least one phosphorus source, at least one mineral source and at least one trace element source is particularly suitable for the microbial culture of gram-positive bacteria. The bacteria cells divide on or in the composition, start to proliferate and the cell clusters start to grow spontaneously. When the composition is in the form of hydrogel the bacteria cells divide in it without the accumulation of cells on the bottom of the cell culture platform. The cells divide homogeneously in the culture media comprising plant derived fibril cellulose. The homogenous dividing of the cells in the fibril cellulose is a prerequisite for the material to function, particularly as 3D microbial culture media.

Fibril cellulose enhances the growth of gram-positive bacteria significantly. A clear synergistic effect was noticed when fibril cellulose was used together with at least one nutrient source comprising at least one carbon source, at least one nitrogen source, at least one phosphorus source, at least one mineral source and at least one trace element source, for the culture of gram-positive bacteria, in an environment necessary for the culture of gram-positive bacteria.

The hydrogel structure enables the bacteria to grow and divide uniformly in the gel matrix without sedimentation or accumulation of the bacteria on the bottom of a vessel, such as a fermentation vessel. The hydrogel is also able to stabilize nutrients, substrates and any other components contained in the composition, or in the fermentation media and prevents possible sedimentation thereof. The properties of the hydrogel may be adjusted according to the needs to more or less viscous by selecting a suitable grade of fibril cellulose or by varying the amount of fibril cellulose in the hydrogel.

The above features are valuable in small scale culture as well as in larger scale culture in fermentation vessels, and particularly in large bioleaching processes where the fibril cellulose hydrogel provides optimal growth environment for the bacteria by preventing the solid mineral/stone substrate from sedimenting. The growth media keeps more homogeneous and the bioleaching process keeps more stable and more easily controllable.

Accordingly, the present invention provides means for the culture of gram-positive bacteria as 2D or 3D microbial culture, where a composition comprising fibril cellulose in combination with at least one nutrient source comprising at least one carbon source, at least one nitrogen source, at least one phosphorus source, at least one mineral source and at least one trace element source, is used.

Fibril cellulose is obtained from any non-animal based cellulose raw material.

The term "cellulose raw material" refers to any cellulose raw material source that can be used in production of cellulose pulp, refined pulp, and fibril cellulose.

The cellulose raw material may be based on any plant material that contains cellulose or any microbial cellulose.

Plant material may be wood and said wood can be from softwood tree such as spruce, pine, fir, larch, douglas-fir or hemlock, or from hardwood tree such as birch, aspen, poplar, alder, eucalyptus or acacia, or from a mixture of softwoods and hardwoods. Non-wood material can be from agricultural residues, grasses or other plant substances such as straw, leaves, bark, seeds, hulls, flowers, vegetables or fruits from cotton, corn, wheat, oat, rye, barley, rice, flax, hemp, manilla hemp, sisal hemp, jute, ramie, kenaf, bagasse, bamboo or reed.

The cellulose raw material may be also derived from the cellulose-producing micro-organism, such as from bacterial fermentation processes. The micro-organisms can be of the genus *Acetobacter, Agrobacterium, Rhizobium, Pseudomonas* or *Alcaligenes*, preferably of the genus *Acetobacter* and more preferably of the species *Acetobacter xylinum* or *Acetobacter pasteurianus*.

The term "cellulose pulp" refers to cellulose fibers, which are isolated from any cellulose raw material using chemical, mechanical, thermo-mechanical, or chemi-thermo-mechanical pulping processes.

Cellulose pulp, which can be pulp of plant origin, especially wood (softwood or hardwood pulp, for example bleached birch pulp) and where the cellulose molecules are oxidized in one of the above-described methods, is easy to disintegrate to fibril cellulose.

The term "fibril cellulose" refers to a collection of isolated cellulose microfibrils (nanofibers) or microfibril bundles derived from cellulose raw material. Microfibrils have typically high aspect ratio: the length exceeds one micrometer while the number-average diameter is typically below 1000 nm, particularly 1-200 nm. The diameter of microfibril bundles can also be larger but generally less than 1 μm. The smallest microfibrils are similar to so called elementary fibrils, which are typically 2-12 nm in diameter. The dimensions of the fibrils or fibril bundles are dependent on raw material and disintegration method.

Fibril cellulose is characterized by very high water retention values, a high degree of chemical accessibility and the ability to form stable gels in water or other polar solvents. Fibril cellulose product is typically a dense network of highly fibrillated celluloses. The fibril cellulose may also contain some hemicelluloses; the amount is dependent on the plant source.

To obtain fibril cellulose mechanical disintegration of cellulose pulp, oxidized cellulose raw material or microbial cellulose is carried out with suitable equipment such as a refiner, grinder, homogenizer, colloider, friction grinder, ultrasound-sonicator, fluidizer such as microfluidizer, macrofluidizer or fluidizer-type homogenizer. Preferably the fibril cellulose is mechanically disintegrated product.

Several different grades of fibril celluloses have been developed using various production techniques. The grades have different properties depending on the manufacturing method, degree of fibrillation and chemical composition. The chemical compositions of the grades also vary. Depending on the raw material source, e.g. HW vs. SW pulp, different polysaccharide composition exists in the final fibril cellulose product. Typically, non-ionic or native or neutral grades have wider fibril diameter while the chemically modified grades are a lot thinner. Size distribution is also narrower for the modified grades.

The term "fibril cellulose" refers here to one grade of fibril cellulose or a combination of two or more different grades of fibril cellulose. For example modified grades of fibril cellulose may be blended with native grade for varying the properties of the gel.

Suitably plant derived native fibril cellulose is used, preferably as an aqueous gel.

Fibril cellulose is understood to encompass here also any chemically or physically modified derivates of cellulose, fibril cellulose or nanofiber bundles, obtained from any cellulose raw materials. The chemical modification may be based for example on carboxymethylation, oxidation, (TEMPO-oxidation), esterification, or etherification reaction of cellulose molecules. Modification may also be realized by physical adsorption of anionic, cationic, or non-ionic substances or any combination of these on cellulose surface. The described modification can be carried out before, after, or during the production of fibril cellulose. Certain modifications may lead to materials that are degradable in human body. Modified grades are typically prepared from bleached pulps. In the modified grades, the hemicelluloses are also modified together with the cellulose domain. Most probably, the modification is not homogeneous, i.e. some parts are more modified than others. Thus, detailed chemical analysis is not possible—the modified products are always complicated mixtures of different polysaccharide structures.

Chemically modified grades, such as anionic and cationic grades typically have their surface charge modified and they may suitably be used as dry powder or an aqueous gel. Suitable fibril cellulose or a combination of different fibril celluloses may de selected and designed.

Dry powders of fibril cellulose may conveniently be manufactured by spray drying and/or lyophilization of suspensions or dispersions containing said fibril cellulose, using any conventional methods known in the art.

The fibril cellulose gel or hydrogel refers here to an aqueous dispersion of fibril cellulose. The fibril cellulose has excellent gelling ability, which means that it forms a gel already at a low consistency in an aqueous medium.

Suitably the cellulose raw material such as cellulose pulp is pretreated with acid and base prior to the mechanical disintegration. The pretreatment is effected by subjecting the cellulose pulp to acid treatment, preferably with hydrochloric acid for removing any positively charged ions having a charge more than +1, followed by treatment with an inorganic base containing positively charged ions having a charge +1, preferably NaOH, where $Na^+$ ions replace the earlier ions. The absence of any positively charged ions having a charge more than +1 is particularly advantageous in life science and molecular biology applications where complex formation of DNA with ions with charges more than +1 can be avoided. The pretreatment provides the final product excellent gelling properties and transparency. The fibril cellulose obtained from pretreated cellulose raw material is referred to here as ion exchanged fibril cellulose.

Microbial purity of fibril cellulose is often essential. Therefore, fibril cellulose may be sterilized prior to use, suitably in gel form. In addition, it is important to minimize the microbial contamination of the product before and during the mechanical disintegration, such as fibrillation. Prior to fibrillation/mechanical disintegration, it is advantageous to aseptically collect the cellulose pulp from the pulp mill immediately after bleaching stage when the pulp is still sterile.

Fibril cellulose hydrogels have typically high yield stress and high zero-shear viscosity at low concentrations. Thus, the hydrogels stabilize effectively solid particles against sedimentation, as is shown in example 6. The same physical features also prevent gas bubbles, possibly formed in the gel, rising from fibril cellulose hydrogels. The buoyancy of gas bubbles can be, however, easily increased by lowering gas pressure (e.g. 15 mmHg) above the gel, which lowers the solubility of gas in the hydrogels phase and, respectively increases the volumes of initial gas bubbles. The increased gas bubbles escape easily to upper gas phase while the cultured microbes remain in the gel phase. This pressure cycle may also be repeated if desire in order to collect the formed gaseous products.

Suitably any grade of fibril cellulose or combinations there of may be used, preferably the native (non-ionic or neutral) grades are used and particularly preferable fibril cellulose is the ion exchanged native fibril cellulose.

The nutrient source is selected according to the specific requirements of each gram-positive bacteria, which is cultured. Particularly, in bioleaching processes the nutrient source includes substrates selected from crushed metal ores to provide valuable metals, such as copper zinc, nickel, cobalt etc.

Optionally further additives well known to a man skilled in the art, generally used in microbial culture of gram-positive microbes may be included in the composition.

The fibril cellulose is suitably used as a hydrogel, film, membrane or plate. The hydrogel may also be obtained by reconstituting a dry powder. The film, plate or membrane may also be reconstituted prior to use by bringing it in contact with water. Particularly the modified grades, such as anionic and cationic grades, may be provided as dry products, such as powders, dry or semi-dry films, sheets or membranes, also as hydrogels. The native and non-ionic grades are preferably provided as hydrogels.

The composition may be provided as a ready-to-use hydrogel, which may be pre-sterilized and packed in sterile packages, or it may be packed as a hydrogel for example in an applicator or container or syringe, which can be used for the application of the gel.

The composition may also be in the form of wet or semi-dry or dry film or plate-like formation or membrane, which may be sterilized. The plates, films or membranes may be produced for example by solvent casting, vacuum pressing, vacuum-filtration, extrusion, or coating methods followed by optional drying to obtain a desired structure. The plate may be used as 2D microbial culture matrix, or alternatively the bacteria inoculum may be blended with a soft hydrogel formed of fibril cellulose, followed by spreading the obtained blend of the plate or membrane.

The number average fibril diameter of the fibril cellulose is suitably from 1 to 200 nm, in one embodiment the number average fibril diameter of native grades is from 1 to 100 nm, and in chemically modified grades from 1 to 20 nm.

The composition comprises from 0.05 to 80 wt % of fibril cellulose. When the composition is a hydrogel, it may comprise from 0.05 to 5 wt %, suitably 0.1-3 wt % of fibril cellulose. A dried composition such as plate or film may comprise higher amounts of fibril cellulose, prior to moisturizing with water, typically up to approximately 95 wt %.

Suitably the composition comprises 0.05-80 wt %, in one embodiment 0.1-50 wt %, particularly 0.1-40 wt %, of the nutrient source comprising at least one carbon source, at least one nitrogen source, at least one phosphorus source, at least one mineral source and at least one trace element source. The high nutrient source refers particularly to bioleaching processes where the metal ore substrate is comprised in the nutrient source.

The composition may optionally comprise one or more additives used in the culture of bacteria. Some examples of said additives are growth factors, inorganic salts, antibiotics etc. generally known in the field.

The composition is obtainable with a method, which comprises the steps of
providing fibril cellulose and at least one nutrient source comprising at least one carbon source, at least one nitrogen source, at least one phosphorus source, at least one mineral source and at least one trace element source;

mixing said fibril cellulose with water and at least one nutrient source comprising at least one carbon source, at least one nitrogen source, at least one phosphorus source, at least one mineral source and at least one trace element source and optional additives to obtain a mixture (composition).

The amount of fibril cellulose in the composition is 0.05 to 80 wt %, and in the composition when hydrogel from 0.05 to 5 wt %, suitably 0.1-3 wt % of fibril cellulose. The amount of the nutrient source is 0.05-80 wt %, suitably 0.1-50 wt % particularly 0.1-40 wt %.

Said mixture may be used as such as a hydrogel, it may be incorporated in a fermentation medium comprising water and/or additives, or alternatively it may be formed to a film, membrane or plate, which may optionally be dried, and any of these may optionally be sterilized. The plates, films or membranes may be produced from the mixture for example by solvent casting, vacuum pressing, vacuum-filtration, extrusion, or coating methods followed by optional drying.

Said composition may suitably be brought into contact with an inoculum of gram-positive bacteria and transferred or placed to an environment for culture of said gram-positive bacteria.

The invention also provides a two-dimensional (2D) or three-dimensional (3D) matrix comprising said composition, and living gram-positive bacteria cells. Preferably the composition in the form of hydrogel is used in a 3D matrix for microbial culture.

The method of using fibril cellulose in a matrix for microbial culture of gram-positive bacteria, comprises the steps of providing living gram-positive bacteria cells,
providing said composition comprising fibril cellulose and at least one nutrient source comprising at least one carbon source, at least one nitrogen source, at least one phosphorus source, at least one mineral source and at least one trace element source, water and optional additives,
incorporating said bacteria cells in and/or on the composition to provide a two-dimensional or three-dimensional arrangement.

The bacteria cells may be cultured in said composition in a two-dimensional and/or three-dimensional arrangement in an environment suitable for culture of gram-positive bacteria.

According to one embodiment the bacteria are aerobic gram-positive bacteria.

The method for culturing gram-positive bacteria comprises the steps of providing living gram-positive bacteria cells,
contacting the cells with said composition comprising fibril cellulose and at least one nutrient source comprising at least one carbon source, at least one nitrogen source, at least one phosphorus source, at least one mineral source and at least one trace element source, water and optional additives, to form a matrix,
culturing the cells within said matrix in a two-dimensional or three-dimensional arrangement in an environment for culture of gram-positive bacteria.

Said composition acts also as an effective growth enhancing additive in microbial culture and in fermentation processes of gram-positive bacteria. Thus the invention also provides means for enhancing the growth of gram-positive bacteria.

Said culturing or fermentation processes may be batch operated or continuous and they may be carried out on a small scale or larger industrial scale, such as fermentation processes, and in very large scale, such as bioleaching processes.

Said matrix may also be used for storage, and transportation of said bacteria, and as immobilization matrix in fermentation processes.

The growth of gram-positive bacteria is enhanced very effectively, when said bacteria are cultured in the presence of a nutrient source and fibril cellulose. Particularly a synergistic effect was noticed, which can be seen from the examples too where Bacillus cereus was cultured with and without fibril cellulose. Fibril cellulose alone does not provide an adequate carbon source, and on the other hand the growth of said bacteria in the presence of a conventional growth medium alone does not provide sufficient growth, but when the fibril cellulose, preferably in the form of hydrogel, is added to the growth medium (nutrient source), even at least 5-fold improvement can be achieved in viable cell count.

The composition may be a ready-to-use hydrogel, which may be sterilized and packed in sterile packages, such as vacuum packed plates, suitable for example for biochemical applications, DNA purification etc, or it may be packed as a hydrogel for example in a syringe, which can be used for the application of the gel.

The 3D structure seems to improve microbial growth under suitable growth conditions particularly with gram-positive bacteria and provides a synergistic effect. The 3D structure provides for free molecular diffusion as well as sufficient support, but on the other hand also sufficient flexibility. The diffusion is highlighted in Example 4.

Microbe cells and nutrients are suspended homogeneously into the continuous hydrogel phase due to mechanical support provided by the fibril cellulose fibers. The remarkably high yield stress stabilizes the microbial cells and the grown cell clusters against sedimentation, as can bee seen in the Example 6. The problem relating to sedimentation and forming of layers with varying concentrations of individual components can be avoided or at least decreased to a significant extent. This also makes it possible to use nutrient sources with limited solubility, for providing slow or controlled release of said nutrient.

The composition may suitably be used in large scale liquid or semi-liquid fermentation processes where industrial enzymes, starter cultures, etc are produced, and also in bioleaching processes, particularly in bioheaps.

Fibril cellulose hydrogels provide properties close to optimal particularly for 3D culturing, such as transparent, non-toxic, highly viscous, high suspending power, high water retention, good mechanical adhesion, non-animal based, insensitive to salts, temperature or pH, not degradable, no autofluorescence, injectable by syringe and transferrable by pumping. Fibril cellulose has negligible fluorescence background due to the chemical structure of the material. Furthermore, said hydrogel is not toxic to the cells.

The composition and matrix is also particularly suitable for storage and transportation of microbes, as well as an immobilization matrix for microbial fermentation and microbial enrichment, without any risk of potential detection or enumeration problems.

As the quantification and enumeration of microbes is normally performed by using real-time PCR (polymerase chain reaction) technique where the microbes are broken down to release their DNA and the DNA is thereafter quantified by using specific oligonucleotide primers, thermo-stable DNA polymerase and appropriate thermal cycler, it is essential that the culture media does not comprise materials which interfere or inhibit the PCR reactions and make microbial quantification unreliable. The culture media according to the invention, comprising plant derived fibril cellulose does not interact or inhibit PCR detection or PCR based microbial enumeration.

Fibril cellulose is inert and gives no fluorescent background and it does not interfere with analysis. The culture media or matrix comprising plant derived fibril cellulose can be injected. This enables very easy transferring of the material without the need to use mechanical measures, such as cutting etc. Injectability is explained by the unique rheological properties of plant derived fibril cellulose. The injection can be performed so that the cells stay stable inside the hydrogel or matrix and are homogeneously distributed in the hydrogel or matrix after injection.

Further, fibril cellulose allows easy inoculation, good growth characteristics, simple detection and uncomplicated colony isolation.

Small quantity or single colony can easily be picked up from the matrix and exposed to metabolic characterization.

On a larger industrial scale microorganisms can be cultured in fermentation vessels or in bioleach heaps in a culture medium comprising liquid components and solid components and the composition of the invention. The hydrogel is able to stabilize the microbes and the nutrients including for example solid substrates in bioleaching processes.

EXAMPLES

The following examples are illustrative of embodiments of the present invention, as described above, and they are not meant to limit the invention in any way.

Materials and Methods a) Fibril Cellulose Samples.

Native fibril cellulose was produced by high pressure homogenization (five subsequent cycles) of highly purified bleached birch pulp, followed by autoclave sterilization. After fluidization, the fibril cellulose was dilute hydrogel (1.8 wt %). Ion-exchanged native fibril cellulose was obtained in a similar manner but additionally prior to fibrillation it was subjected to acid-base treatment in order to remove high valency cations (method described in previous sections). After high pressure homogenization (15 subsequent cycles) the ion-exchanged fibril cellulose forms a strong hydrogel having lower turbidity compared to the other sample. Fibril cellulose was sterilized by autoclaving when necessary. Transparent anionic fibril cellulose was obtained as hydrogel (0.9 wt %) by similar homogenization process of a chemically modified cellulose pulp (TEMPO-oxidized cellulose pulp).

b) Microbial Strain and Cultivation.

In all experiments fresh overnight cultures of aerobic gram-positive Bacillus cereus were used in the inoculation. The inoculation cultures did not contain fibril cellulose. The microbial cultivation was performed under optimal conditions and growth media, tryptic soy broth (TBS).

c) Microbial Detection.

Microbial growth was detected visually when colony formation was noticeable. The traditional bacterial cell number determination by plating method was applied.

d) Membranes.

Fibril cellulose membranes were prepared by vacuum filtration of aqueous 0.2 wt % native fibril cellulose dispersion. After filtration, the wet membranes were dried under weight in oven at 55° C. for 48 h. The dry films were smooth and opaque with the grammage of 70-80 g/m$^2$.

Example 1

Fibril Cellulose as a Sole Energy Source for Bacteria

The manufacturing processes of fibril cellulose may comprise steps that increase the risk for microbial contamination. Therefore, plant derived native fibril cellulose was tested for its capability to support microbial growth as a sole energy source. In FIG. 1 plant derived the fibril cellulose was challenged with microbial contamination source (*B. cereus*). In the beginning (0 h) and after overnight incubation on fibril cellulose are presented graphically together with control without the bacteria. The reference bacterial cells were incubated on fibril cellulose overnight and the bacterial cell numbers were counted. Furthermore, the extent of contamination was high, over $10^6$-$10^7$ cells/ml (Rough estimate of cell number can be calculated by dividing the 16S gene number by 10). The results clearly indicate that the strain *B. cereus* does not have any growth on fibril cellulose. However, the control without any microbial inoculation shows high value in PCR analysis, which may be due to earlier contamination of dead microbes or an artefact caused by cellulose fibrils. The fibril cellulose as a sole energy source does not support microbial growth effectively.

Example 2

Effect of Fibril Cellulose on Growth of *Bacillus cereus*

Bacterial attachment to solid support is known to increase their growth rate with some strains. Typically the solid support is two-dimensional, like agar plate surface, instead of three-dimensional, like a matrix comprising fibril cellulose hydrogel. Therefore, *Bacillus cereus* strain was tested for its ability to grow on normal optimal culture medium with and without fibril cellulose.

Very good results were obtained with *B. cereus* strains, measured either with viable count or with quantitative PCR.

Figure 2:
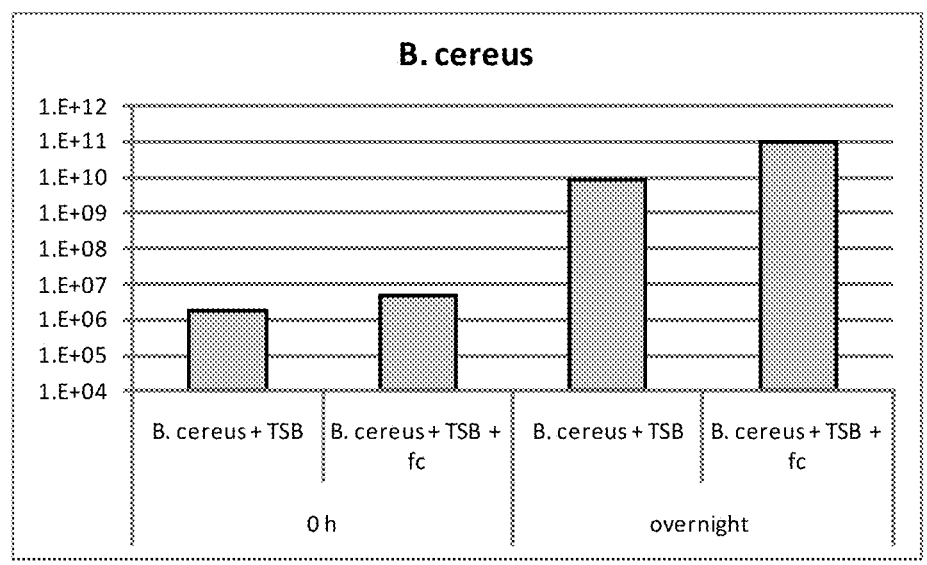
FIG. 2 illustrates graphically *Bacillus cereus* viable counts (colony forming units/ml) from pure cultures on different matrices.
Figure 3:
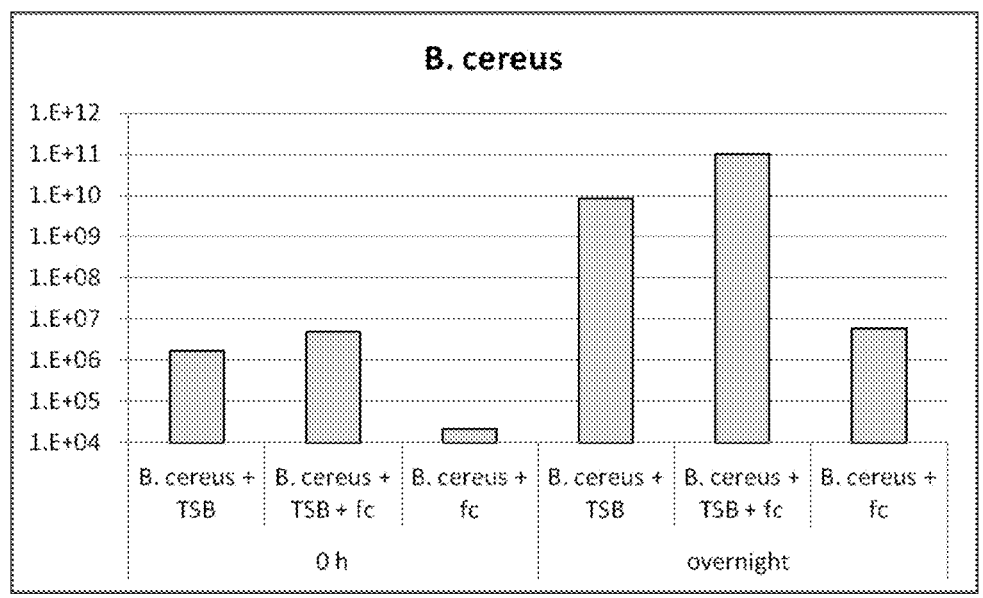
FIG. 3 illustrates *Bacillus cereus* enumeration results of PCR assays.
Figure 4:
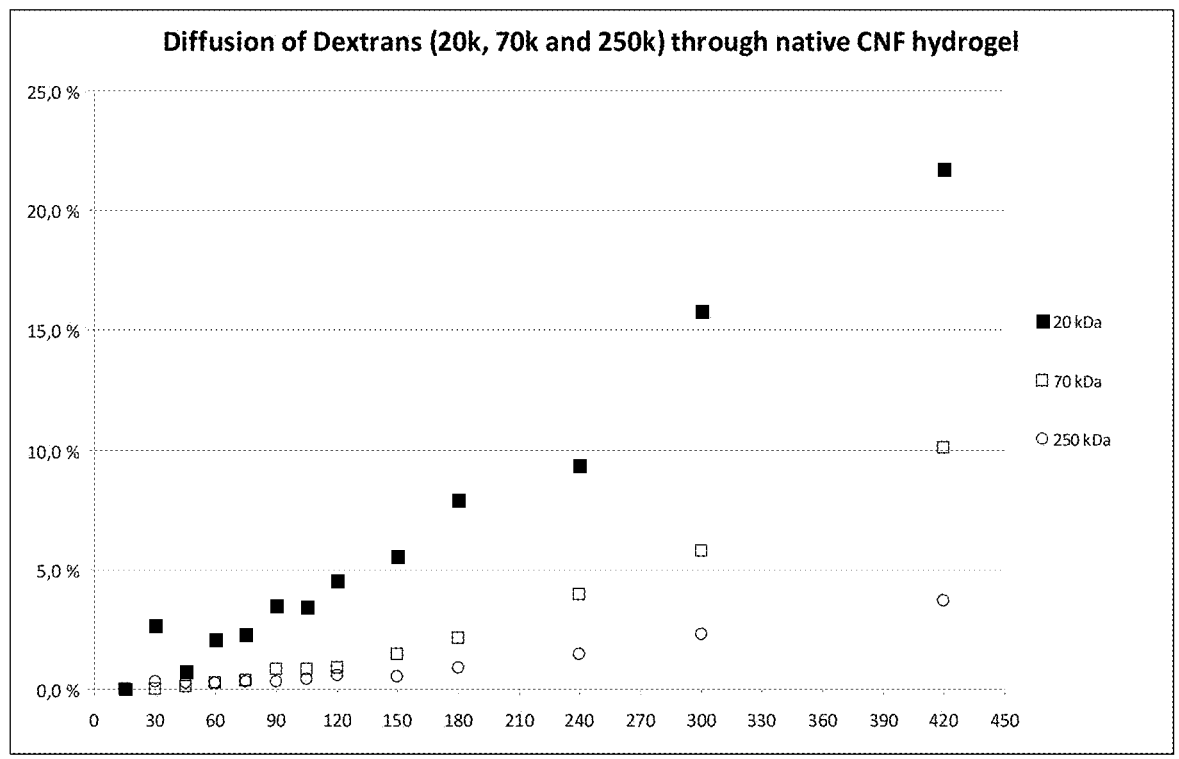
FIG. 4 depicts diffusion of different molecular weight dextrans (20 kDa, 70 kDa, and 250 kDa) through 1% native cellulose nanofiber hydrogel.
Figure 5:
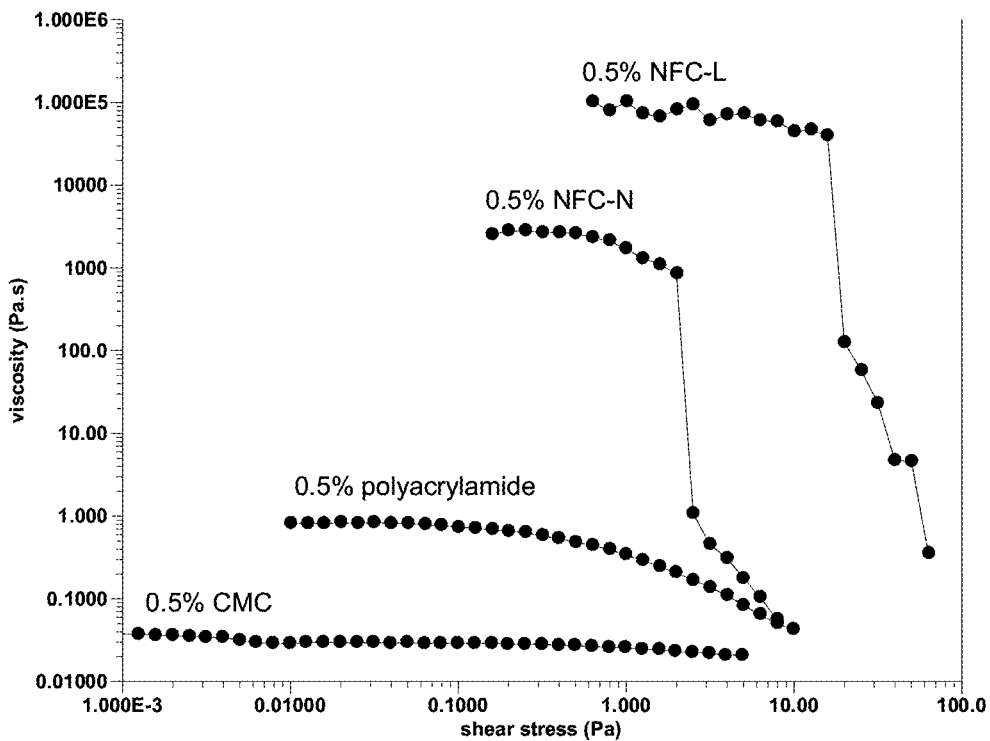
FIG. 5 depicts viscosity of 0.5% fibril cellulose hydrogels as function of applied shear stress in comparison with 0.5% solution of water soluble polymers polyacrylamide (5000 kDa) and CMC (250 kDa).

Table 1 below lists the results from the experiment where pure culture of *B. cereus* grown overnight on the tryptic soy broth (TSB) medium in the presence of 1.5 wt % of native fibril cellulose and without it. It is clear that fibril cellulose alone does not yield significant growth i.e. it does not provide adequate carbon source for *B. cereus*. However, TSB supplemented with the fibril cellulose gives five times higher viable cell count when compared to TSB alone. This indicates that plant derived fibril cellulose in the growth medium improves microbial yields and increases growth rates. Similar trial was carried out with qPCR detection instead of the viable cell counting as presented in FIG. 2, where *Bacillus cereus* viable counts (colony forming units/ml) from pure cultures on different matrices were provided. It verifies the previous finding and provides even higher yield in the presence of fibril cellulose (over logarithmic unit difference). The three dimensional structure seems to improve microbial growth under optimal growth conditions particularly with gram+ bacteria and provides a synergistic effect.

TABLE 1

Bacillus cereus viable counts from pure cultures on different matrices

| Matrix | colony forming units/ml |
|---|---|
| Fibril cellulose | ~2 × 10$^4$ cfu/ml |
| Fibril cellulose and TSB-media | ~3 × 10$^8$ cfu/ml |
| TSB-media | ~7 × 10$^7$ cfu/ml |

Example 3

Enumeration of Microorganisms from Fibril Cellulose Carrier

*Bacillus cereus* bacterium was cultivated in two different culture media, one containing 1.5 wt % of plant derived native fibril cellulose and one without it. PCR based enumeration was used in this experiment and it provided excellent example of fibril cellulose's interaction with the PCR detection.

The growth medium used in the experiment was standard trypsin soy broth, and it was prepared according the manufacturer's instructions and autoclaved for sterility. Before autoclaving the culture medium was divided into two parts, to one of which 1.5% by weight of fibril cellulose was added. Small inoculum of *B. cereus* was grown overnight at 37° C. to reach dense microbial culture, and that was used for the inoculation of both culture media, about thousand fold dilution was used in the inoculation. Both test culture media were sampled at 0 and 24 hours after the inoculation. 0.1 ml sample of each culture was used for PCR based microbial enumeration. The enumeration method was based on the Ruminolyze protocol, where the microbial sample was first diluted to washing buffer, and microbial cells were pelleted by centrifugation (10 min 18000×g). The supernatant was discarded and pellet was suspended to enzymatic lysis buffer and thereafter strongly beaten with glass beads in order to both enzymatically and mechanically lyse the microbial cells to release their DNA content. The released DNA was purified with phenol-chloroform extraction, then precipitated with ethanol and finally dissolved to the DNA storage buffer. The *B. cereus* enumeration was performed with two *B. cereus* selective DNA primers and Sybergreen I chemistry. The results are presented in FIG. 3.

Accordingly *Bacillus cereus* cell numbers on culture media comprising tryptic soy broth (TSB) and fibril cellulose (fc) in the beginning (0 h) and after overnight incubation were analyzed by quantitative PCR. This experiment indicates that small number of *B. cereus* cells, about $10^5$ cells/ml can be detected in the presence of fibril cellulose. This shows that fibril cellulose has no effect on the sensitivity of the PCR assay. Furthermore, 24 hour sample gives higher cell numbers than the 0 hour sample. This means that the dynamic range of PCR is not disturbed by the presence of fibril cellulose and the fibril cellulose does not hinder the PCR reaction when is it run at its maximum speed, in other words when there are large amounts of template DNA. FIG. 3 also shows that more cells are counted in the presence of fibril cellulose at both 0 hours and 24 hours sampling points. This suggests that fibril cellulose aids the DNA isolation and provides higher DNA yields for *B. cereus* enumerations. This also suggests that fibril cellulose even improves PCR protocols.

Example 4

Diffusion of Dextrans Through Fibril Cellulose Hydrogels

Detailed knowledge on the diffusion properties of a cell culture material is important. The cell culture material should be porous enough to allow diffusion of nutrients and oxygen to the cultured cells as well as to enable efficient diffusion of metabolites from the cells. The diffusion properties of fibril cellulose hydrogel were demonstrated with different molecular weight dextrans in the following manner:

400 μl of anionic (oxidized) or native fibril cellulose (1%) was planted per filter on the apical compartment in Transwell™ filter well plates (filter pore size 0.4 μm). 1 ml of PBS was added into the basolateral side and 100 μl (25 μg) of fluorescent labeled dextrans were added on top of the hydrogels (MW of 20 k, 70 k and 250 k). Plate was fixed firmly and left undisturbed on a well plate rocker. 100 μl samples were taken from the basolateral side and equal amount was replaced with PBS. First samples were taken with 15 minute intervals, other samples were taken with different time points ranging from 30 minutes to 2 hours and final samples at 24 hours. Total of 168 samples were taken. Target plate (OptiPlate™-96 F) was measured at excitation and emission wavelengths 490 nm and 520 nm respectively.

Diffusion of different molecular weight dextrans through 1% native cellulose nanofiber gel is presented in FIG. 4. The diffusion of the model compounds takes place at constant rate and it is highly dependent on the molecular weight (size) of the compound. It is clear that in the fibril cellulose hydrogels molecules are able to diffuse efficiently although the gel structure is firm enough to stabilize the cell suspension.

Example 5

Flow Properties of Fibril Cellulose Hydrogel

The rheological flow properties of fibril cellulose hydrogels show several features that are beneficial in the cell culture use. The hydrogels have a high viscosity at low shear (or rest) for optimum suspending capacity of the cells but also show shear-thinning behavior at higher shear rates to enable easy dispensing and injection. The ability of fibril cellulose to provide these kinds of rheological properties was demonstrated in a test series where the viscosity of fibril cellulose dispersions was measured over a broad shear stress (rate) range in a rotational rheometer (AR-G2, TA Instruments, UK).

Fibril cellulose dispersions show much higher zero-shear viscosities (the region of constant viscosity at small shear stresses) than other water soluble polymers, as shown in FIG. 5. The zero-shear viscosity of fibril cellulose is greatly increased by smaller nanofibril diameter induced by preceding chemical pretreatment of the starting material. The stress at which shear-thinning behavior starts ("yield stress") is also considerably high for the fibril cellulose dispersions. The suspending ability of a material is the better the higher the yield stress. The cells are effectively stabilized against sedimentation by the combined effects of high zero-shear viscosity and high yield stress and high storage modulus. The gravitational force applied by the cells is much weaker than the yield stress. Thus, the suspended cells are "frozen" inside the gel matrix if mixing with fibril cellulose or "frozen" on the gel if deposited on the top of the gel.

In FIG. 6 the viscosity is presented as a function of the measured shear rate. From this FIG. 6 it is obvious that the viscosity of the fibril cellulose dispersions drops at relatively small shear rates and reaches a similar level as that measured for the reference materials at shear rates of about 200 s−1.

Figure 6:
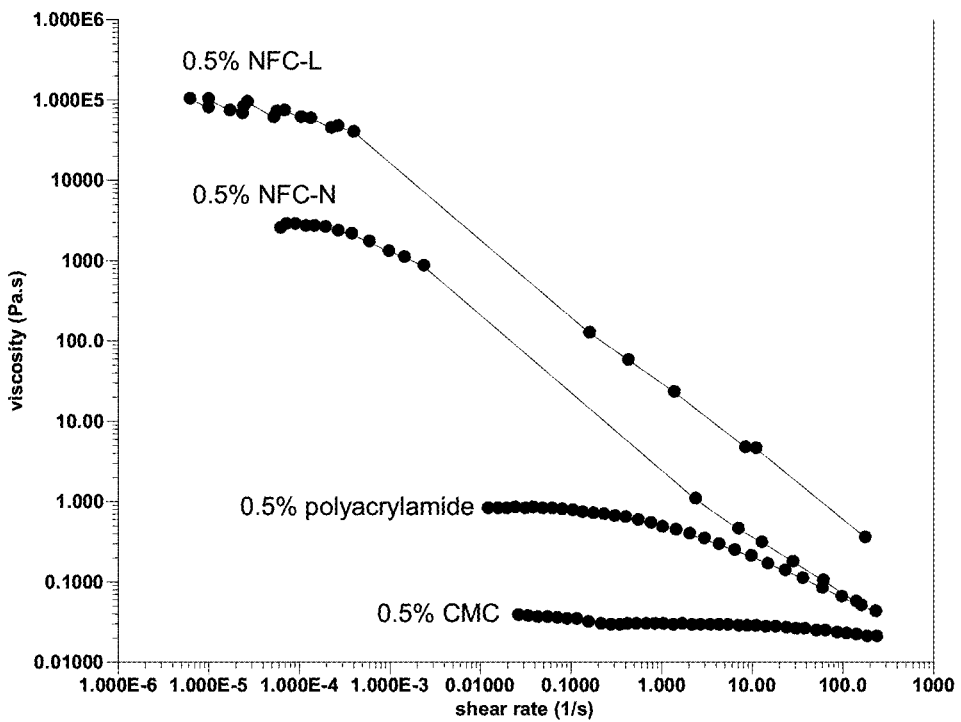
FIG. 6 depicts viscosity of 0.5% CNF hydrogels as function of measured shear rate in comparison with 0.5% polyacrylamide and CMC. Typical shear rate regions of different physical processes have been marked on the figure with arrows.
Figure 7:
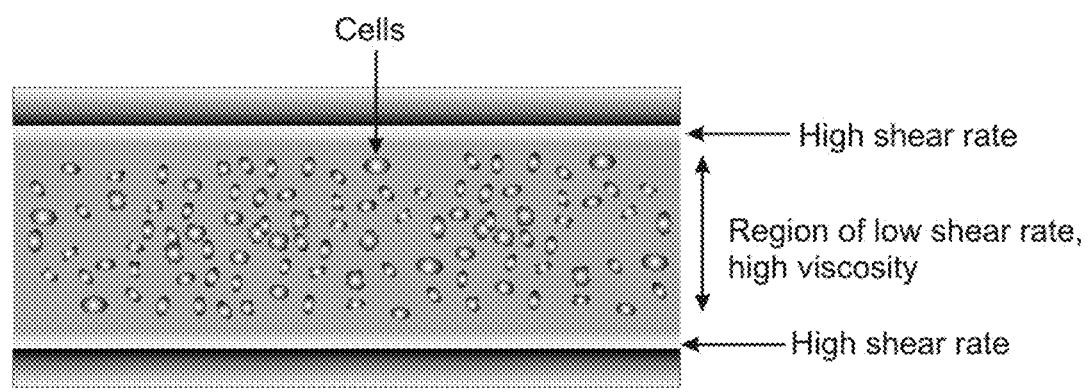

The network structure of fibril cellulose breaks down upon shearing (FIG. 6). Upon the application of a certain stress, the viscosity of the system drops dramatically and a transition from solid-like to liquid-like behavior occurs. This kind of behavior is beneficial as it enables mixing of the cells homogeneously into the fibril cellulose suspension by moderate mechanical shearing. When two-phase liquids, such as flocculated fibril cellulose dispersions, are sheared (e.g. in a rheometer or in a tube), the dispersed phase tends to move away from the solid boundaries, which leads to the creation of a lower-viscosity layer of liquid at the walls of the container (FIG. 7). This phenomenon means that the resistance to flow, i.e. the viscosity is lower at the boundaries than in the bulk of the dispersion. Respectively, injection of the fibril cellulose hydrogel with a syringe and a needle or with pipette is easy even at high concentrations (1-4%). The phenomenon enables also easy dispensing of cell suspensions with minimum disturbance of the cells, i.e. majority of the cells are located in the middle of the needle and are practically at rest (FIG. 7).

Example 6

Stability

Even very dilute dispersions of fibril cellulose have a very high viscosity at low shear rates. The hydrogel structure is also recovered when shear, such as injection, ceases. At static conditions, fibril cellulose forms a hydrogel network with high elastic modulus and exceptionally high yield stress. Due to these properties, fibril cellulose has a very high suspending power of solid particles even at very low concentration.

Figure 8:
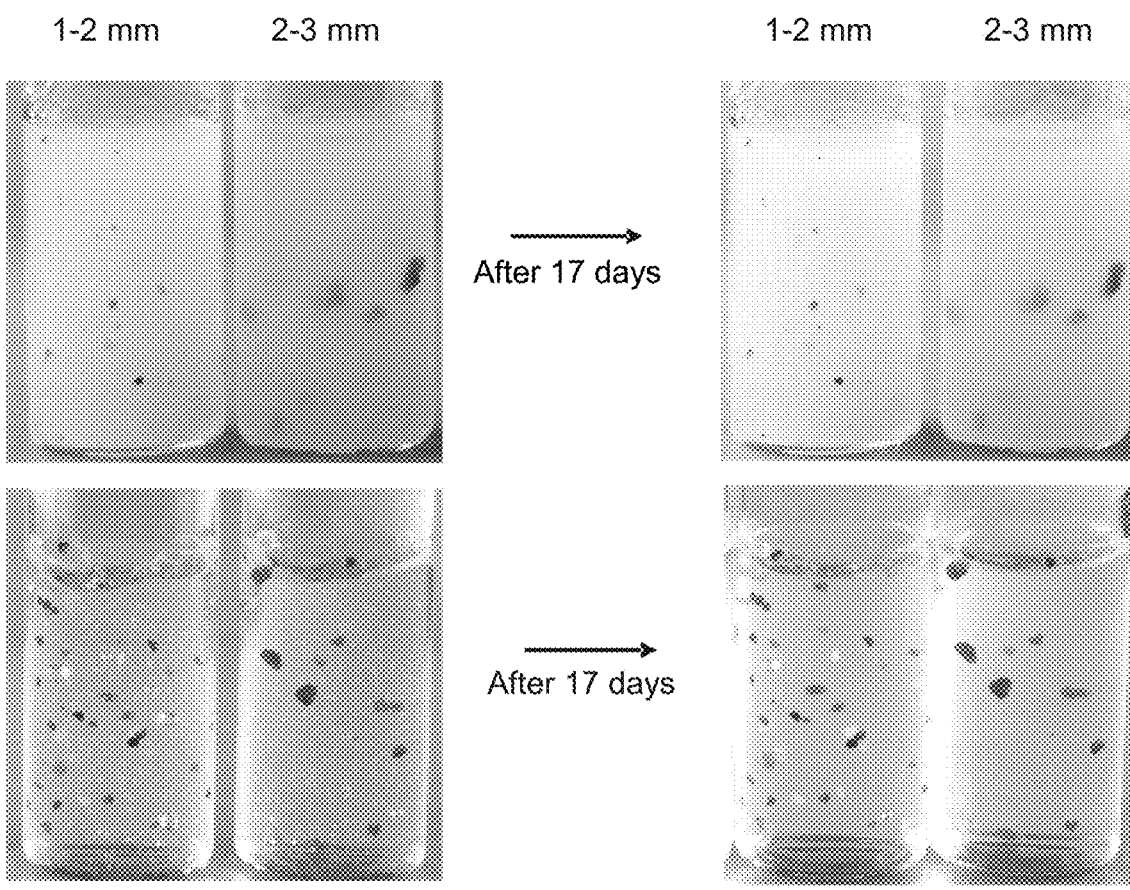

The suspending ability at static conditions is demonstrated with gravel suspensions. 0.5% dispersions of native fibril cellulose and anionic fibril cellulose are able to stabilize even 2-3 mm size gravel particles for very long periods of time, see FIG. 8. It should be noted that the anionic fibril cellulose is able to stabilize particle suspensions at lower concentration than native fibril cellulose.

While the invention has been described with respect to specific examples including presently preferred modes of carrying out the invention, those skilled in the art will appreciate that there are numerous variations and permutations of the above described embodiments that fall within the spirit and scope of the invention. It should be understood that the invention is not limited in its application to the details of construction and arrangements of the components set forth herein. Variations and modifications of the foregoing are within the scope of the present invention.

The invention claimed is:

1. A three-dimensional matrix for microbial culture of gram-positive bacteria, said matrix comprising:
mechanically disintegrated nanofibrillar cellulose and at least one nutrient source comprising at least one carbon source, at least one nitrogen source, at least one phosphorus source, at least one mineral source and at least one trace element source, wherein the matrix is a hydrogel matrix comprising 0.1-3 wt % of nanofibrillar cellulose; and
living gram-positive bacteria cells suspended homogenously in the hydrogel matrix,
the hydrogel matrix having a yield stress sufficient to provide mechanical support for stabilizing the bacteria cells to uniformly grow and/or divide therein and for inhibiting sedimentation thereof, wherein the matrix has a liquid viscosity upon shearing such that the matrix is dispensible, pumpable, or injectable, the mechanically disintegrated nanofibrillar cellulose being formed using a refiner, a grinder, a homogenizer, a colloider, a friction grinder, an ultrasound-sonicator, a fluidizer, or a fibrillator.

2. The matrix according to claim 1, wherein the nanofibrillar cellulose is selected from plant derived nanofibrillar cellulose and microbial nanofibrillar cellulose.

3. The matrix according to claim 1, wherein the nanofibrillar cellulose is selected from native nanofibrillar cellulose and chemically modified nanofibrillar cellulose.

4. The matrix according to claim 1, wherein the nanofibrillar cellulose is native ion-exchanged nanofibrillar cellulose.

5. The matrix of claim 1, wherein the at least one nutrient source has limited solubility.

6. The matrix according to claim 1, wherein the hydrogel matrix is a direct product of homogenization and fluidization of said nanofibrillar cellulose.

7. The matrix according to claim 1, wherein the nanofibrillar cellulose is plant-derived nanofibrillar cellulose.

8. The matrix of claim 1, wherein the nanofibrillar cellulose is configured to form a stable gel in a polar solvent.

9. A method for the manufacture of a three-dimensional matrix for microbial culture or fermentation of gram-positive bacteria, said method comprising:
providing living gram-positive bacteria;
mixing mechanically disintegrated nanofibrillar cellulose with water and at least one nutrient source comprising at least one carbon source, at least one nitrogen source, at least one phosphorus source, at least one mineral source and at least one trace element source to obtain the matrix, wherein the matrix comprises 0.1-3 wt % of nanofibrillar cellulose;
suspending the bacteria homogenously in the matrix, wherein the matrix has a liquid viscosity upon shearing such that the matrix is dispensable, pumpable, or injectable, the mechanically disintegrated nanofibrillar cellulose being formed using a refiner, a grinder, a homogenizer, a colloider, a friction grinder, an ultrasound-sonicator, a fluidizer, or a fibrillator.

10. The method according to claim 9, wherein the nanofibrillar cellulose is selected from plant derived nanofibrillar cellulose and microbial nanofibrillar cellulose.

11. The method according to claim 9, wherein the nanofibrillar cellulose is selected from native nanofibrillar cellulose and chemically modified nanofibrillar cellulose.

12. The method according to claim 9, wherein the nanofibrillar cellulose is native ion-exchanged nanofibrillar cellulose.

13. The method according to claim 9, wherein the matrix is formed as a film, membrane, plate, or powder which is optionally dried.

14. The method according to claim 9, wherein the matrix is sterilized.

15. A method for culturing or fermenting living gram-positive bacteria cells, wherein the living bacteria cells are incorporated in the hydrogel matrix of claim 1 to form a blend, which is then spread on a membrane, film, or plate and cultured or fermented.

16. The method according to claim 15, wherein the culture or fermentation is carried out in a fermentation vessel.

17. The method according to claim 15, wherein the culture or fermentation is carried out as bioleaching process.

* * * * *